(12) United States Patent
Kluge et al.

(10) Patent No.: US 8,236,021 B2
(45) Date of Patent: Aug. 7, 2012

(54) HANDHELD DEVICE FOR THE REPETITIVE LOCAL PUNCTURING OF A SKIN FOR AN INPUT OF A LIQUID ACTIVE SUBSTANCE

(75) Inventors: Jörn Kluge, Teltow (DE); Kristian Plückhahn, Berlin (DE)

(73) Assignee: MT Derm GmbH, Berlin (DE)

( * ) Notice: Subject to any disclaimer, the term of this patent is extended or adjusted under 35 U.S.C. 154(b) by 700 days.

(21) Appl. No.: 11/878,645

(22) Filed: Jul. 25, 2007

(65) Prior Publication Data

US 2008/0033470 A1 Feb. 7, 2008

(30) Foreign Application Priority Data

Jul. 25, 2006 (EP) .................................... 06015461

(51) Int. Cl.
*A61B 17/34* (2006.01)
(52) U.S. Cl. ...................................................... 606/185
(58) Field of Classification Search .......... 606/184–186, 606/167, 169, 177–179; 600/564, 566, 567, 600/583; 604/264–272; 81/9.22
See application file for complete search history.

(56) References Cited

U.S. PATENT DOCUMENTS

| 4,671,277 | A | 6/1987 | Beuchat |
| 4,798,582 | A | 1/1989 | Sarath et al. |
| 5,054,339 | A | 10/1991 | Yacowitz |
| 5,114,045 | A * | 5/1992 | Herpe .............................. 222/105 |
| 2002/0069726 | A1 | 6/2002 | Adler et al. |
| 2006/0200180 | A1 * | 9/2006 | Lee ................................ 606/169 |

FOREIGN PATENT DOCUMENTS

| DE | 299 16 971 U | 1/2000 |
| EP | 0269164 A1 | 6/1988 |
| GB | 1154388 A | 6/1969 |
| WO | WO 2004/075971 A | 9/2004 |

* cited by examiner

*Primary Examiner* — Ryan Severson
*Assistant Examiner* — Ashley Cronin
(74) *Attorney, Agent, or Firm* — Smith Patent Office (57) ABSTRACT

The invention relates to a handheld device for the repetitive local puncturing of a skin for an input of a liquid active substance, particularly a permanent make-up and tattoo handheld device, with: a piercing device formed in a needle module with repetitive movement forwards and backwards, which piercing device is driven with the help of a drive unit formed in a drive module, a reservoir for the liquid active substance, a pump system coupled to the reservoir where the said pump system is configured in order to discharge the liquid active substance held in a cavity of the reservoir by means of pressure application, and a fluid connection running at least partially in a needle module casing where said fluid connection is configured in order to supply the liquid active substance from the reservoir to the piercing device.

21 Claims, 9 Drawing Sheets

HANDHELD DEVICE FOR THE REPETITIVE LOCAL PUNCTURING OF A SKIN FOR AN INPUT OF A LIQUID ACTIVE SUBSTANCE

The invention relates to a handheld device for the repetitive local puncturing of a skin for an input of a liquid active substance, particularly a permanent make-up and tattoo handheld device.

BACKGROUND OF THE INVENTION

Devices for the controlled piercing of an object are used, for example, for the purpose of injecting an active substance into an object. The term "active substance" adopted here is to be understood in very general sense. It can be preferably a medical or a cosmetic active substance. Included also are all types of vaccines as well as coloring materials such as, for example, tattoo coloring materials or coloring materials for permanent make-up. The substance can also be dermal fillers or substance used in a treatment known as carboxy therapy.

With the use of such handheld devices, the active substance is to be brought to the piercing device in such a way that the active substance can be entered when puncturing the skin. This is normally performed with known handheld devices in that the user of the handheld device immerses the needle and also the needle nozzle, as desired, through which the needle moves during the repetitive forward and backward movement, into a supply of the liquid active substance. This immersion process is then carried out repeatedly during the usage of the handheld device. It can be envisaged in this case that a cavity is formed behind the needle nozzle and already beginning in the zone of the needle nozzle, as desired, into which cavity the liquid active substance moves during the immersion process into the supply because of capillary forces so that during the usage of the handheld device the needle, at least in sections, moves repeatedly through the cavity with the liquid active substance and subsequently entrains the liquid active substance.

The document DE 299 16 971 U1 describes the use of a removable color cartridge as a reservoir for a coloring material used for permanent make-up or for applying a tattoo.

The document U.S. Pat. No. 4,798,582 envisages the supply of a coloring material for a tattoo handheld device from a reservoir to the piercing device via a valve, which on its part is opened and closed with the help of a ball that moves during operation the handheld device.

Furthermore, the document U.S. Pat. No. 4,671,277 describes the use of a color tank which is arranged on a needle module so that a coloring material can be supplied to the piercing device from the color tank through a fluid connection. The fluid connection contains a wire that moves when operating the handheld device so that coloring material can makes its way from the color tank to the piercing device.

The document U.S. Pat. No. 5,054,339 describes a tattoo device in which the coloring material is supplied to the piercing device from an external coloring material container which is a line system coupled to the tattoo device.

Finally, a handheld device for the repetitive local puncturing of a skin is known from the document WO 2004/075971 A1 with which a liquid active substance can be brought into the skin. With the known handheld device, a syringe is externally arranged on a casing, which syringe forms a reservoir for the liquid active substance. The syringe is activated with a drive so that the liquid active substance is conducted to the piercing device via a syringe dispenser line.

SUMMARY OF THE INVENTION

The object of the invention is to create a handheld device for the repetitive local puncturing of a skin for an input of a liquid active substance, wherein a controlled discharge of the liquid active substance is enabled.

This object is solved according to the invention by means of a handheld device according to the present invention. Advantageous embodiments of the invention are the subject-matter of the dependent claims.

The invention comprises the conceptual idea of providing a handheld device for the repetitive local puncturing of a skin for an input of a liquid active substance, particularly a permanent make-up and tattoo device, with: a piercing device formed in a needle module with repetitive movement forwards and backwards, which apparatus is driven with the help of a drive unit formed in a drive module, a reservoir for the liquid active substance, a pump system coupled to the reservoir, where said pump system is configured in order to discharge by means of pressure application the liquid active substance held in a cavity of the reservoir, and a fluid connection that is at least partially running in a needle module casing where said fluid connection is configured to supply the liquid active substance from the reservoir to the piercing device.

With the help of the pump system, both the quantity as well as the timing for the discharge of partial volumes of the liquid active substance can be individually determined for random applications. In addition to this and with the help of the active discharge resulting from the pressure application, which insofar can also be described as pumping, there is a reduction of the probability that the liquid active substance during usage does not make its way at all to the piercing device, as is frequently the case with the state of the art, if the passively effected flow to the piercing device is interrupted because of contamination or blockage. The formation of the fluid connection at least partially in the needle module casing additionally has the advantage of a space-saving implementation, a fact that supports the miniaturization of the handheld device in particular. Furthermore, the handling convenience of the handheld device is improved by the casing integration.

Depending on the type of handheld device and with this particular method, various types of liquid active substances can be brought from the reservoir to the piercing device, for example a coloring material during the application of permanent make-up or tattoos, medical active substances such as vaccines or even cosmetic active substances. Under normal circumstances, the liquid active substance will distribute itself on the piercing device, at least partially wetting the same. It can be envisaged that the reservoir has an opening for the intake of air during the discharge of the liquid active substance. The opening is preferably executed as a vent valve.

A further development of the invention preferably envisages that the reservoir extends longitudinally along an axis in the movement direction of the piercing device during the forward and backward movement. This supports a narrow embodiment of the handheld device to the best possible extent.

It can be envisaged with an advantageous embodiment of the invention that the fluid connection extends at least partially along the axis running in the movement direction of the piercing device during the forward and backward movement. Not only with this embodiment, the fluid connection can be formed in the form of one or several fluid channels. The liquid active substance then makes its way to the piercing device through the outlet of the fluid channels. The outlet of the fluid connection is preferably formed in the zone of a needle nozzle at the needle module, through which the piercing device moves during the repetitive forward and backward movement, which can be envisaged not only with a channel-type embodiment of the fluid connection. Alternatively or complementarily, an outlet of the fluid connection can be formed in a zone behind the needle nozzle in the needle module.

A further development of the invention can envisage that the reservoir is formed at least partially encasing the axis running in the movement direction of the piercing device during the forward and backward movement.

A preferred further development of the invention envisages that the fluid connection, at least with one section running in the needle module casing, is formed at least partially encasing the axis running in the movement direction of the piercing device during the forward and backward movement.

With a purposeful embodiment of the invention it can be envisaged that the reservoir is detachably mounted and is executed as a disposable reservoir, as desired.

An advantageous embodiment of the invention envisages that the reservoir is formed in a detachably mounted reservoir module encompassing at least parts of the pump system.

A further development of the invention preferably envisages that the pump system is separated in a fluid tight manner from the cavity holding the liquid active substance. By means of the fluid-tight separation of pump system and the cavity holding the liquid active substance, a resulting and possible damaging of the pump system with the liquid active substance is prevented. This configuration also supports the exchangeability of the reservoir and a repeated usage of the pump system related thereto.

With an advantageous embodiment of the invention it can be envisaged that, at the reservoir, a displaceable component is formed at least section-wise for the transmission of the pressure application generated by the pump system onto the liquid active substance. In a possible embodiment, and with the use of the displaceable component, pressure is applied directly or indirectly to the liquid active substance in order to bring it out of the reservoir. Following pressure application the displaceable component is normally moved backwards and this takes place either with the help of a separately available return force, for example, by means of a spring, or by means of a backhaul movement provided by the pump system. In this way, both a sustaining pressure application as well as an impulse-type pressure application are made possible.

A further development of the invention can envisage that the at least section-wise displaceable component is an elastically deformable component and is executed as an elastic membrane, as desired. A preferred embodiment of the elastically deformable component is a foil made from a synthetic material, which can, for example, also be adhesively applied.

A preferred further development of the invention envisages that the elastically deformable component is an elastically deformable wall section, which is formed in the zone of the cavity, as desired.

With a purposeful embodiment of the invention it can be envisaged that the at least section-wise displaceable component is formed at least partially encasing the axis running in the movement direction of the piercing device during the forward and backward movement.

An advantageous embodiment of the invention envisages that a push tappet of the pump system is allocated to the at least section-wise displaceable component.

A further development of the invention preferably envisages that the push tappet is formed in the drive module.

It can be envisaged with an advantageous embodiment of the invention that the push tappet is a ring tappet at least partially encasing the axis running in the movement direction of the piercing device during the forward and backward movement.

A preferred further development of the invention envisages that the pump system is configured in order to periodically transport the liquid active substance from the reservoir to the piercing device via the fluid connection.

A preferred further development of the invention can envisage that the reservoir is formed in a main body and the pump system coupled to the reservoir has a rotatable rotor component located in the reservoir and, during the turning movement, strokes over one or several main body openings which are in union with the fluid connection. With the stroking over of the one or several main body openings, partial volumes of the liquid active substance are pressed into the openings in order to conduct these partial volumes to the piercing device. During the turning movement in the reservoir, the partial volumes are entrained by the rotor component and then pressed into the one or several main body openings. In one embodiment, one or several wing sections are formed at the rotatable rotor component on the side facing the one or several main body openings, wherein said wing sections stroke over the main body openings. The reservoir in the main body component can be closed off in a further development at least partially liquid-tight against the ambient space by means of a sealing membrane. A driving of the turning movement of the rotor component and, subsequently, of the pressure application of the liquid active substance for discharge through the main body openings is effected preferably in a non-contact manner, for example by means of a magnetic drive.

It can be envisaged with a purposeful embodiment of the invention that a control apparatus coupled to the pump system is envisaged, and is configured in order to correspondingly excite the pump system of the repetitive forward and backward movement of the piercing device. The control apparatus can be integrated in the needle module or in the drive module. With the help of the control apparatus, electronic information on the repetitive forward and backward movement of the piercing device is processed for the purpose of generating control signals for the pump system, so that this can be excited in dependence of the repetitive forward and backward movement of the piercing device. It can be envisaged that the excitation of the pump system is performed, for example, from a certain position of the piercing device during the forward and backward movement. However, the excitation of the pump system can also be envisaged in a certain ratio to the number of the forward and backward movements of the piercing device. For example, the pump system in one embodiment is excited only every n (n=1, 2, . . . ) extension movements of the piercing device. In a purposeful embodiment the control apparatus is integrated at least partially in a control unit, to which the device is connected, in particular in order to provide for the voltage supply of the drive unit. By way of the control unit, and in a preferable manner, the user is also given the possibility of regulating the excitation of the pump system according to user input. In this case the user, in accordance with the application, can take into consideration the parameters of the liquid active substance, particularly its viscosity and/or of the puncturing process where different skin types have to be considered, for example.

An advantageous embodiment of the invention envisages that the reservoir is formed on the needle module.

A further development of the invention can envisage that the pump system implements at least one drive mechanism generating the pump impulses, selected from the following group of drive mechanisms: piezo mechanism, magnetic drive mechanism and micro pump mechanism. The implementation of one or several drive mechanisms leads to individual advantages in each case, resulting from the specific mode of the implemented drive mechanism(s). The piezo mechanism can be implemented a way as known from its use in principle in conjunction with inkjet printers. A magnetic drive mechanism has the advantage in that a non-contact pump impulse transmission can take place in this case. Micro pump mechanisms are particularly suitable for a miniaturized embodiment. Non-contact drive mechanisms are particularly preferred in such cases where mechanical wear is avoided and a low-noise operation is supported.

A preferred further development of the invention envisages that the needle module is detachably coupled to the drive module and is executed as a disposable module, as desired.

With a purposeful embodiment of the invention it can be envisaged that the fluid connection leads to at least one section of the piercing device, selected from the following sections of the piercing device: an outer needle surface, a needle intermediate space formed between several needles, and an internal needle cavity. The piercing device can be designed in various modes. First of all, there is the option of using a single needle. However, the use of a needle system having several needles can also be envisaged. Cannulas can be used both in single as well as in multiple needle systems. The single needle or the multiplicity of needles are normally accommodated in a needle shaft, onto which the driving force generated by the drive unit is exerted in order to provide for the forward and backward movement of the piercing device. Drive units and coupling mechanisms for transmitting the drive force onto the piercing device are known to the those skilled in the art in various designs and, for this reason, do not require any further detailed description here.

DESCRIPTION OF PREFERRED EMBODIMENT EXAMPLES OF THE INVENTION

The invention is described as follows in greater detail on the basis of preferred embodiment examples with reference to the Figures of a drawing. The Figures show the following.

Figure 1:
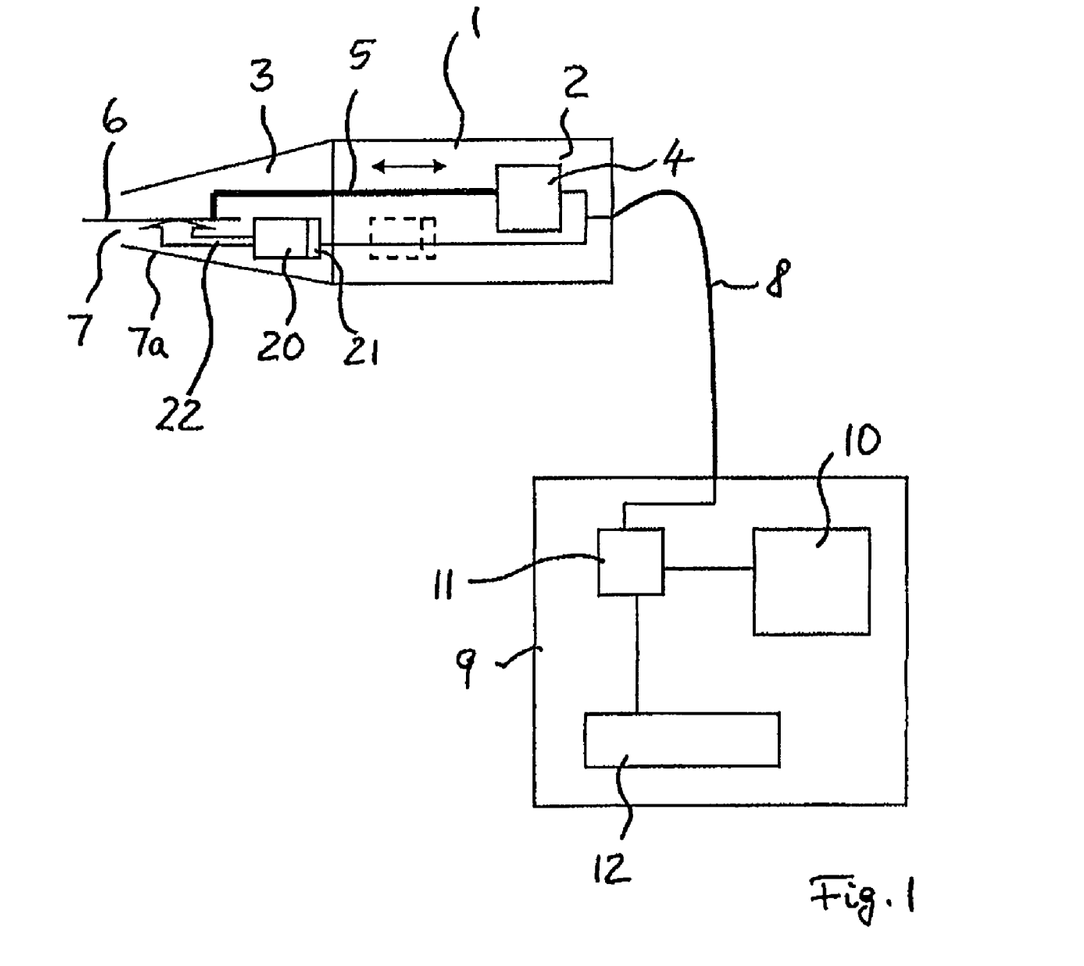
FIG. 1 a schematic illustration of a handheld device for the repetitive local puncturing of a skin, which is connected to a control apparatus.

FIG. 1 shows a schematic illustration of a handheld device 1 for the repetitive puncturing of a skin. The handheld device 1 comprises a drive module 2 and a detachable needle module 3 coupled thereto. In the drive module 2 an electric motor 4 as a driving device is envisaged which couples to a needle 6 by way of a coupling mechanism 5 which preferably comprises, on its part, a wobble disk mechanism. The needle 6 forms a piercing device for skin puncturing which is also formed in other embodiments by a system containing several needles. With the help of the electric motor 4 and the coupling mechanism 5, a repetitive drive movement is generated which is conducted onto the needle 6 by way of the coupling mechanism 5, so that the needle 6 is moved forwards and backwards through an opening 7 of the needle module 3. Normally, the needle 6 is coupled to the coupling mechanism 5 by means of a needle shaft (not shown). A needle nozzle is formed at the casing sections 7a of the needle module 3 adjacent to the opening 7.

The needle 3 is detachably connected to the drive module 2, for example by means of a screw connection, a plug-in or a clamp connection. This method allows the user to detach the needle module 3, preferably executed as a disposable module, from the drive module 2 and to replace it after use. In this case the needle module 3 is executed in such a way that it can be detached as an overall module from the drive module 2. The needle module 3 is made available preferably as a sterilized component in a suitable package.

The handheld device 1 is connected to a control apparatus 9 via a connecting line 8. With the help of the connecting line 8, the connection of the electric motor 4 to a voltage supply (not shown) is effected in particular. In addition, the connecting line 8 in the illustrated embodiment comprises one or several lines for the transmission of electronic data. In alternative embodiments, the handheld device 1 can be connected with the control apparatus 9 by way of a cordless data connection. A voltage supply of the handheld device 1 can be carried out in one embodiment with the help of a rechargeable battery integrated in the handheld device 1.

In the control apparatus 9, a display device 10, a control device 11 and an operating device 12 are formed. Further components or assembly groups can be envisaged in the control apparatus 9 but are not shown here for the purpose of simplification of the illustration. With the help of the operating device 12, the user can enter predefined data for the operation of the handheld device 1, for example on the key panel or with the help of rotary knobs. By way of the display device 11, information on the operation of the handheld device 1 are shown, for example an adopted operating mode, a selected piercing frequency or similar. Even the display of information concerning the currently used needle module 3 can be envisaged. The control device 10 serves the particular purpose of controlling the operation of the handheld device 1, but also the purpose of the co-ordination of the display on the display device 11.

In the needle module 3 a reservoir 20 in the form of a container or a cavity is formed, which serves the purpose of holding the liquid active substance that is discharged in controlled quantities during the use of the handheld device 1. A pressure or pump system 21 is allocated to the reservoir 20 with which pressure is applied to the liquid active substance which is subsequently taken out of the reservoir 20 by way of a fluid connection 22, executed for example as a channel, and can be brought to the needle 6. In the embodiment as shown in FIG. 1, the reservoir 20 is formed in the needle module 3. It can also be envisaged to have the pump system 21 and/or the reservoir 20 arranged in the drive module 2, and this is shown in FIG. 1 in an embodiment by means of a dashed box.

Figure 2:
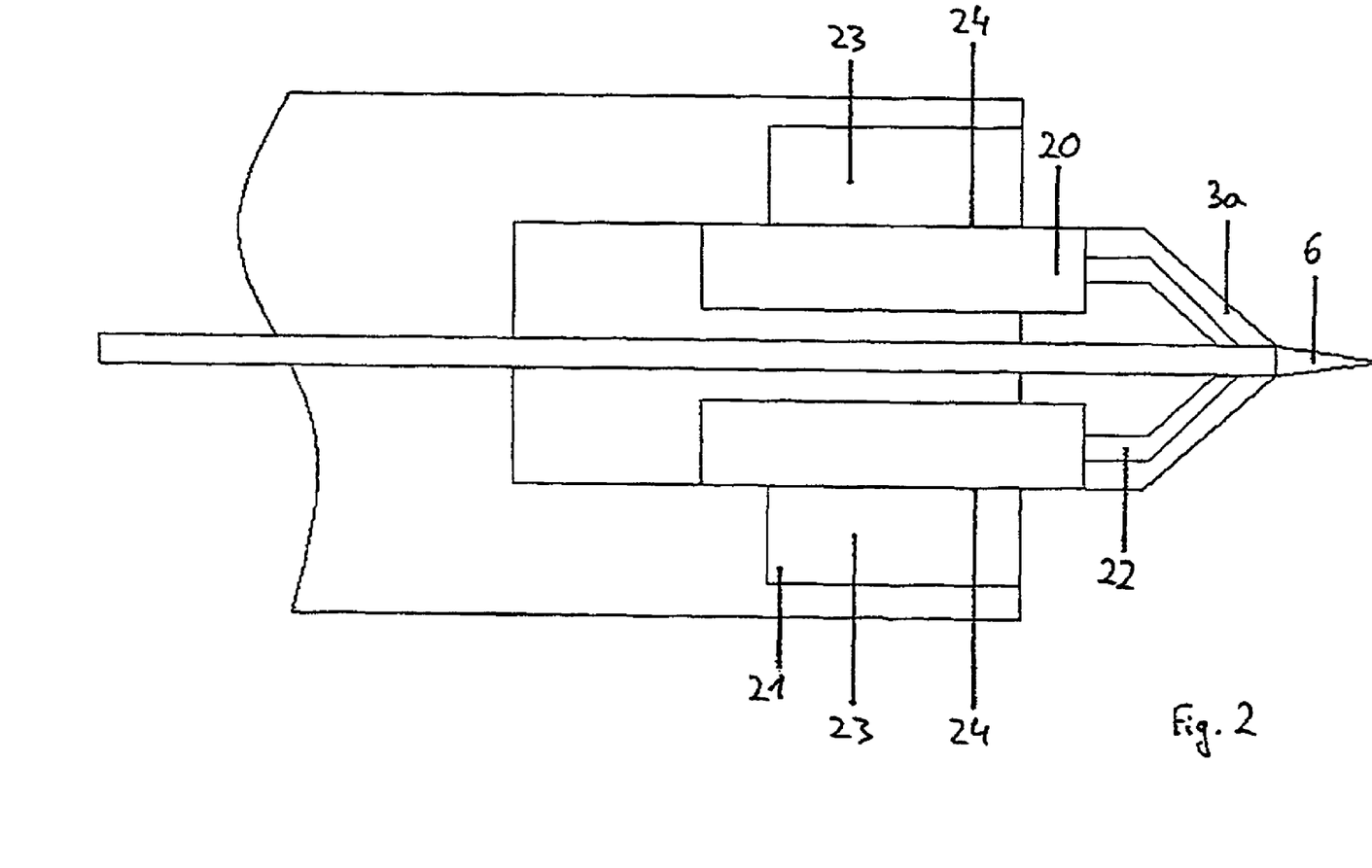
FIG. 2 a section of the handheld device shown in FIG. 1 in cross-sectional view, where a piezo pressure mechanism is used for discharge a liquid active substance from a reservoir and bringing it to the needle.

FIG. 2 shows a section of a handheld device in FIG. 1 in cross-sectional view in which a piezo pressure mechanism is used for discharging a liquid active substance from a reservoir and leading it to the needle.

The reservoir 20 with the liquid active substance is formed around the needle 6. The liquid active substance flows from the reservoir 20 to the needle 6 through the fluid connection 22 running in a needle module casing 3a. The pump system 21 is formed with the help of one or several piezo actuators 23, which are excited with electric signals, in order to produce a pressure to be applied to the reservoir 20. For this purpose the reservoir 20 is formed from a deformable material in the zone of a wall section 24, for example an expandable membrane which is pressed into the reservoir 20 when pressurized by the piezo actuators 23, either in an impulse-type or rather continual mode. As a result, a partial volume of the liquid active substance is pressed into the fluid connection 22. With the embodiment as shown in FIG. 2 the piezo actuators 23 enclosed by the pump system 21 are arranged in the zone of the needle module 3 and, subsequently, are exchangeable together with this.

Figure 3:
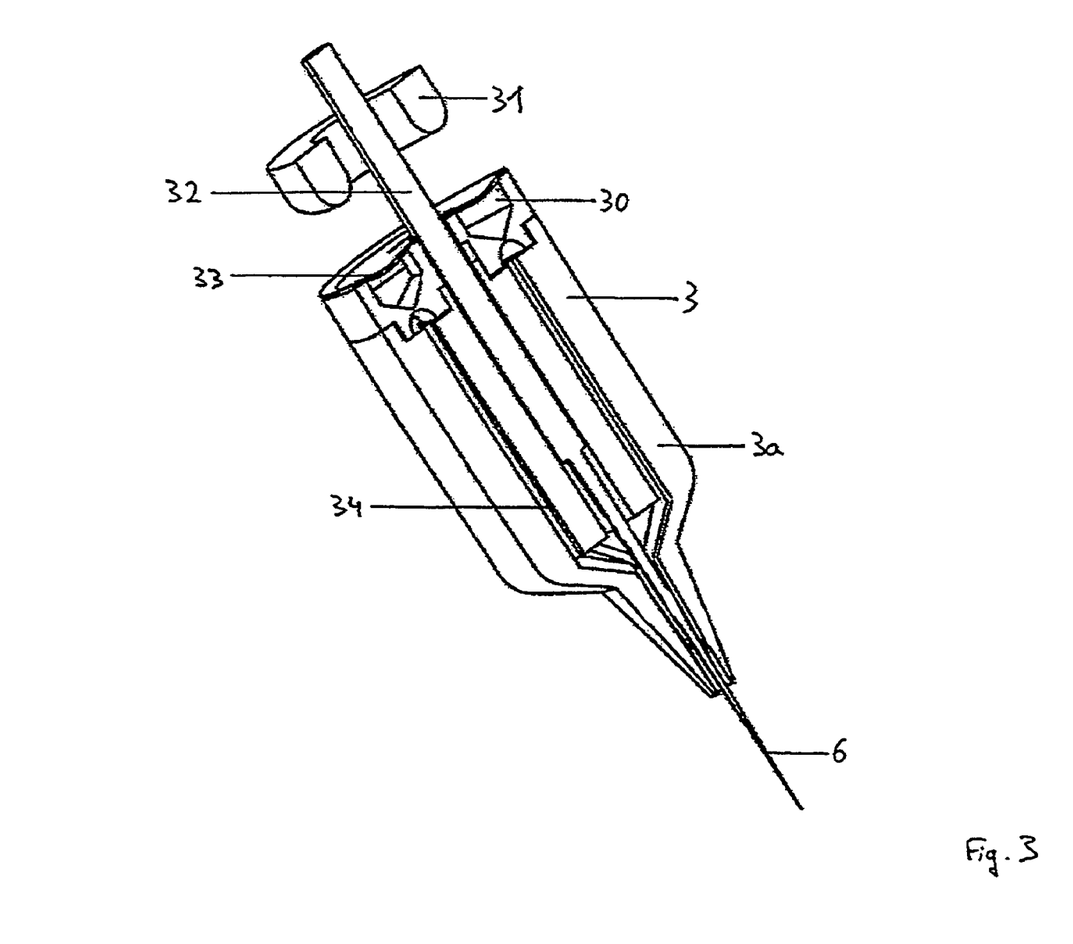
FIG. 3 a further embodiment of a section of the handheld device in FIG. 1 in the cross-sectional view, with which a pressure application is brought in from a pump system by way of a tappet for the purpose of discharging the liquid active substance from the reservoir.

FIG. 3 shows a further embodiment of a section of the handheld device in FIG. 1 in cross-sectional view in which pump pressure of a pump system is applied by way of a tappet in order to discharge the liquid active substance from the reservoir. In FIG. 3, the same reference numbers are used for the same features, as in the preceding FIGS. 1 and 2.

The reservoir 20 is formed with the help of a cavity 30. As part of the pump system 21, a ring tappet 31 is shown in this embodiment which tappet encases a needle shaft 32. The ring tappet 31 is also moved forwards and backwards along an axis parallel to the movement direction of the needle 6 during the forward and backward movement. If the ring tappet 31 is moved towards the cavity 30, it establishes contact in a limit position with an elastic membrane 33 covering off the cavity 30 and presses the elastic membrane 33 into the cavity 30 containing the liquid active substance. In this way, the liquid active substance in the cavity 30 is applied with pressure, either for continual discharge or in an impulse-type mode, and pressed into a fluid connection 34 which supplies the active substance to the needle 6.

Figure 4:
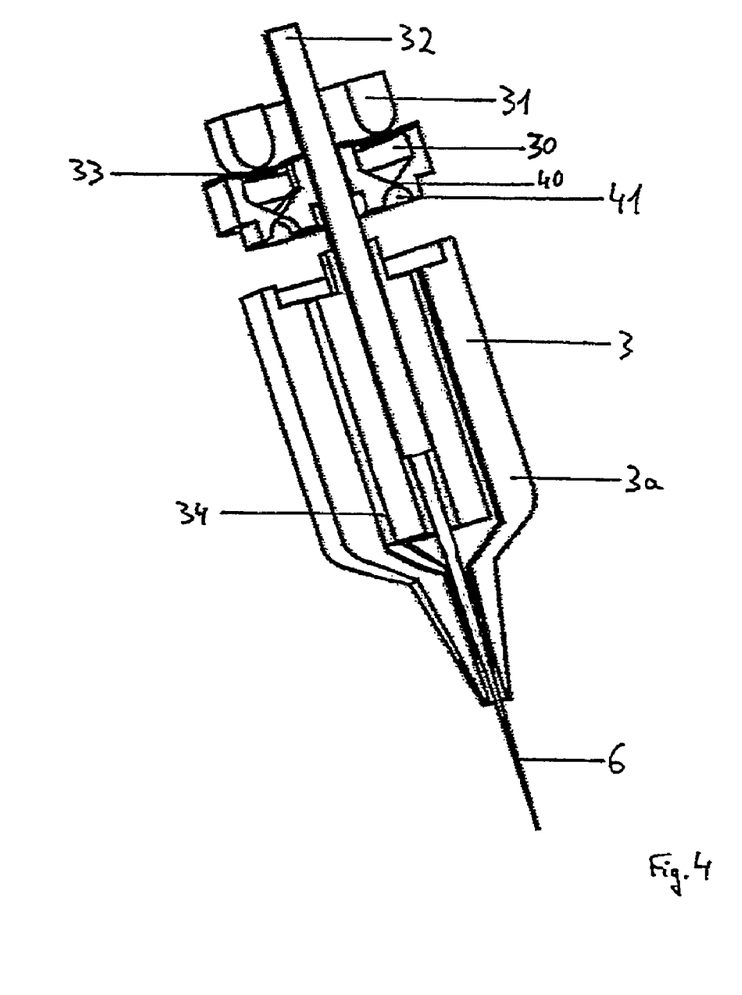
FIG. 4 a further illustration of the embodiment according to FIG. 3.
Figure 5:
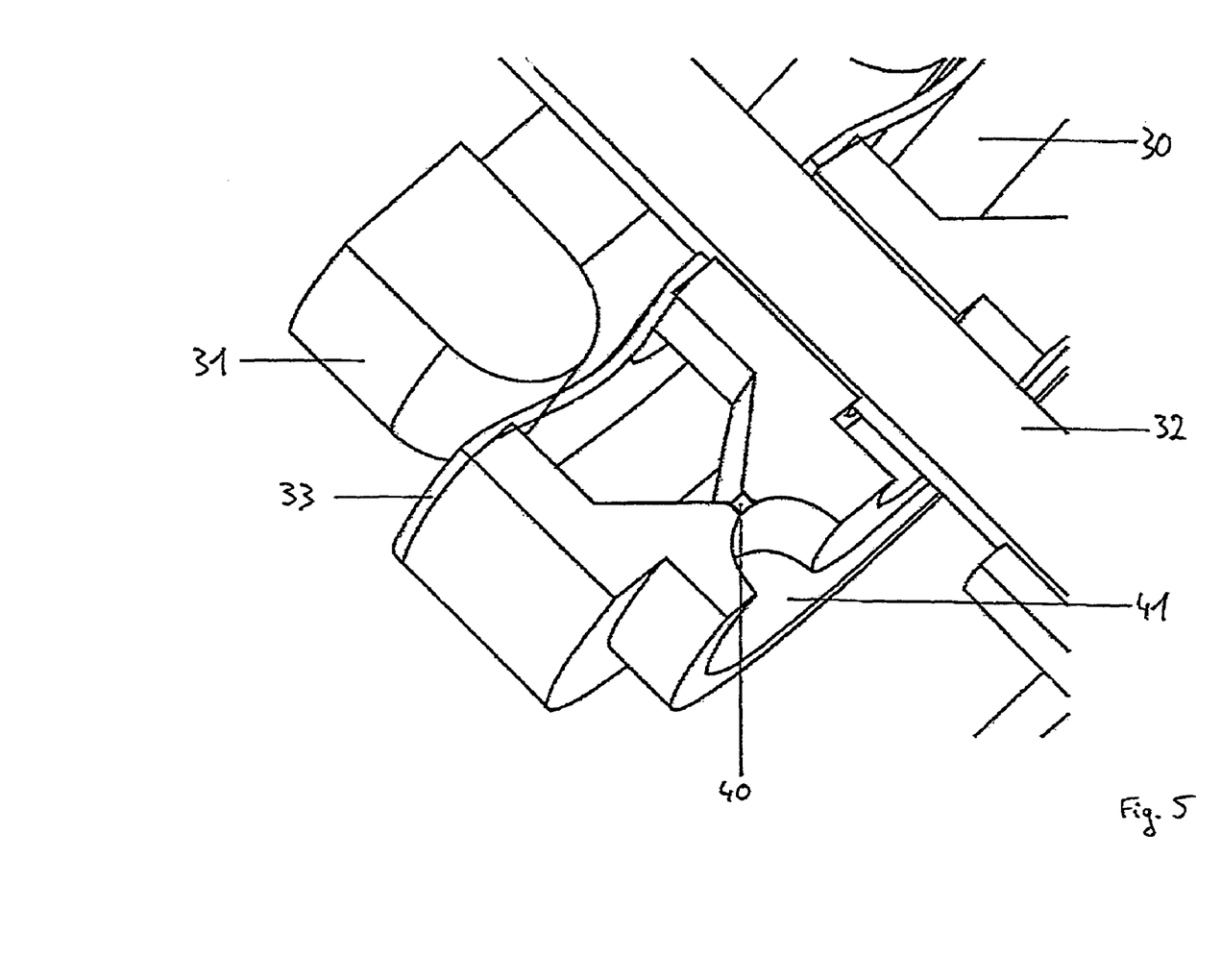
FIG. 5 a section of the illustration in FIG. 4 in detail.

FIGS. 4 and 5 show further details of the embodiment according to FIG. 3. In the FIGS. 4 and 5 the same reference numbers are used for the same features, as in FIG. 3.

The resulting effect is that the cavity 30 with the liquid active substance is joined with the fluid connection 34 to the needle 6 by way of bores 40 and a distributing groove 41, and said fluid connection then conducts the pumped liquid active substance to the needle 6. The distributing groove 41 serves the purpose of conducting the liquid active substance into several channel-type bores of the fluid connection 34.

The ring tappet 31 can be actuated in the pump system with the help of various drive mechanisms. These include an electromagnetic drive with coil and anchor. The electromagnetic drive can be used for the pre-tensioning of a spring (not shown) which clamps between electromagnetic drive and ring tappet 31 in order to move the ring tappet 31 in this way.

A piezo mechanism can also be used in order to move the ring tappet 31 in order to produce the pressure application. Furthermore, the drive of the ring tappet 31 can be carried out with the help of a compressed air mechanism where the ring tappet 31 forms a working piston in a cylinder (not shown), wherein a return force for the ring tappet 31 can be provided with the help of a spring. In a similar way it can be envisaged to drive the ring tappet 31 as a working piston in a cylinder (not shown) on the basis of a hydraulic mechanism, wherein again a return force is provided with a spring, as desired.

Figure 6:
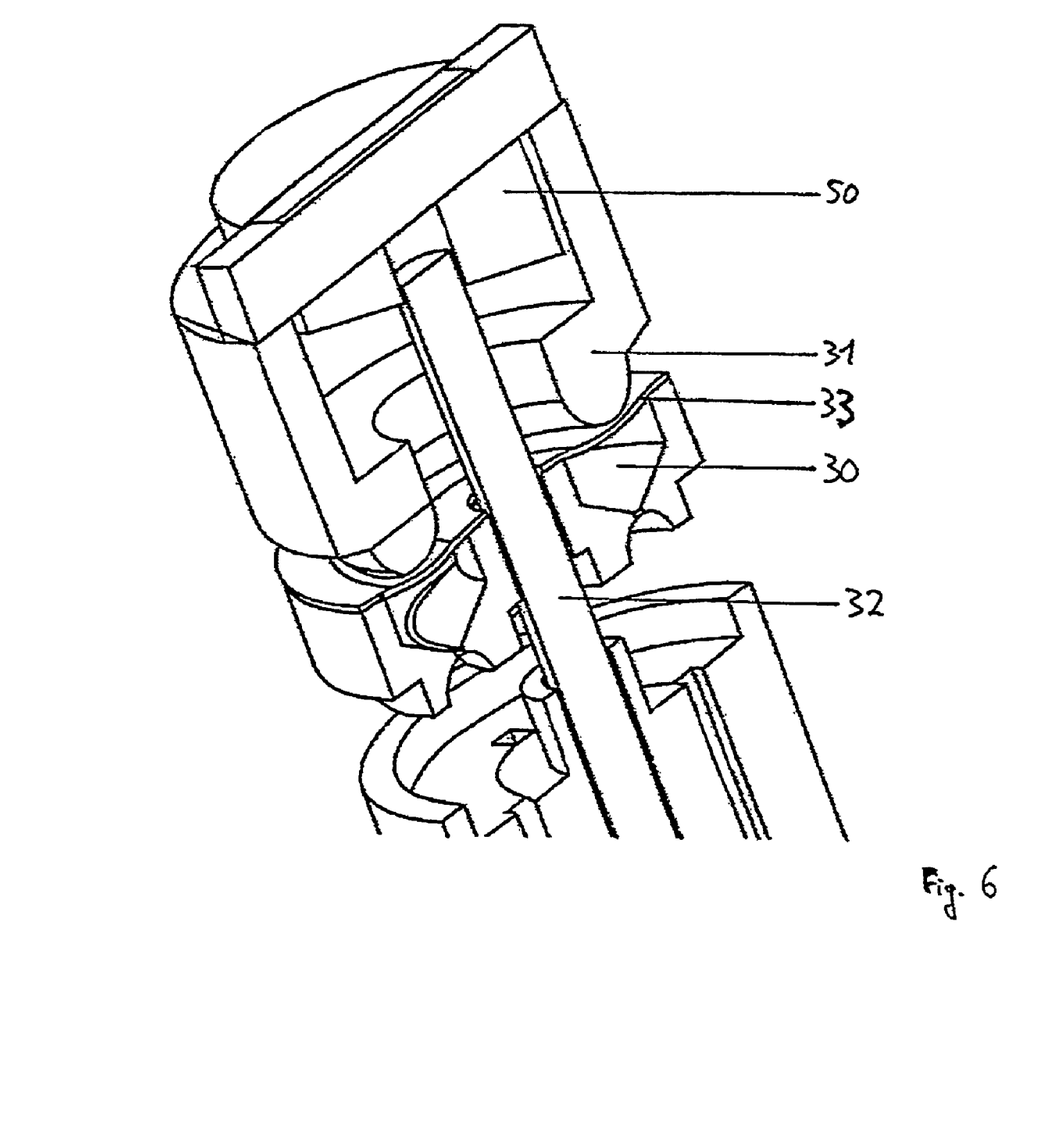
FIG. 6 a design of the embodiment according to FIG. 3 to FIG. 5 in the cross-sectional view, where a magnetic drive mechanism is formed in the pump system.

FIG. 6 shows a design of the embodiment according to the FIGS. 3 to 5 in cross-sectional view, where a magnetic drive mechanism is formed in the pump system. A magnet 50 is turned, which produces an alternating magnet field in this way, through which the ring tappet 31, which also has magnets, is periodically applied with a repelling force. The ring tappet 31 is pre-tensioned with a spring for the purpose of return movement. The magnets can be mounted in such a way that these are moved away from the axis of rotation as a result of the centrifugal forces.

Figure 7:
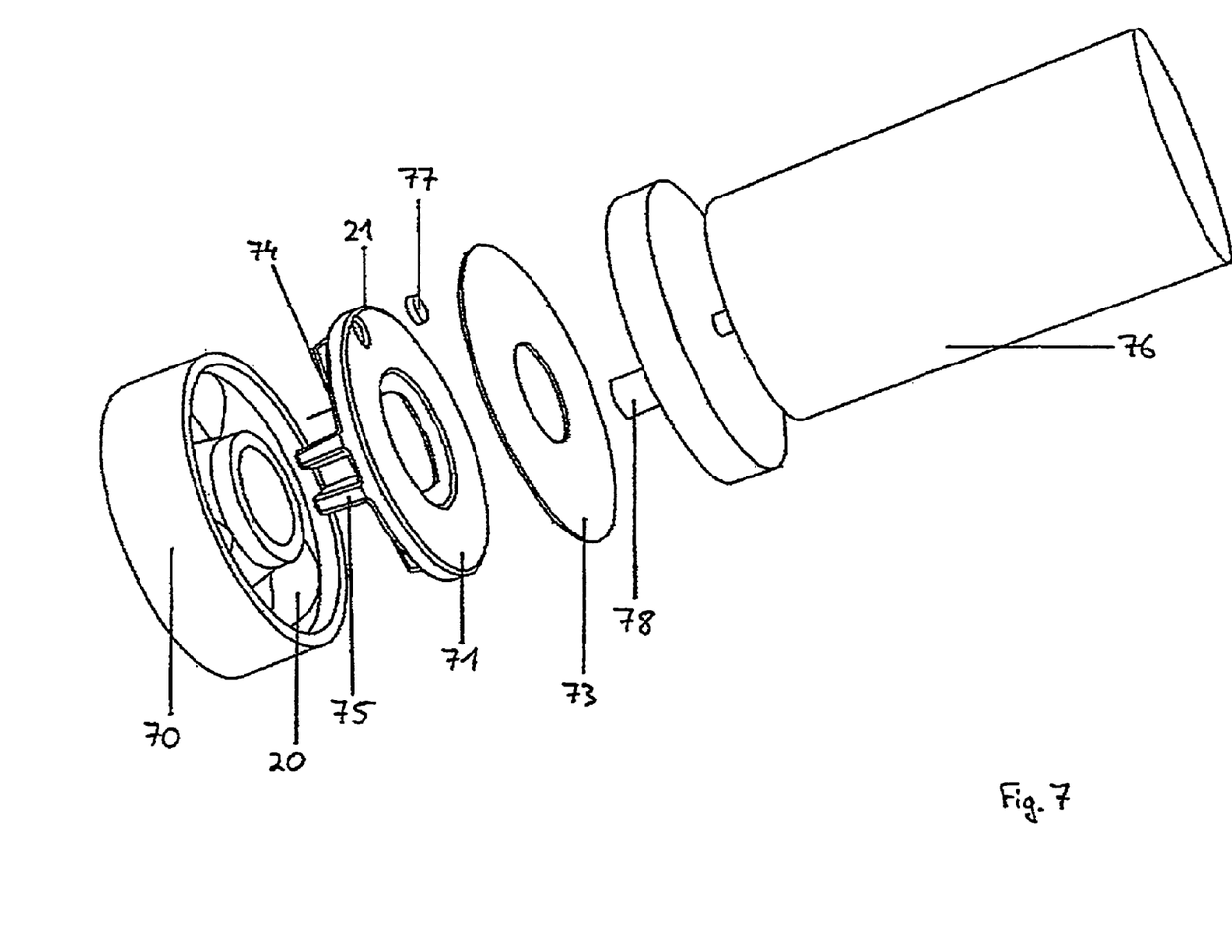
FIG. 7 another embodiment of a section of the handheld device in FIG. 1 in perspective illustration, with which the pumping pressure of a pump system is generated by means of a rotor component in a main body for the purpose of discharging the liquid active substance from the reservoir.
Figure 8:
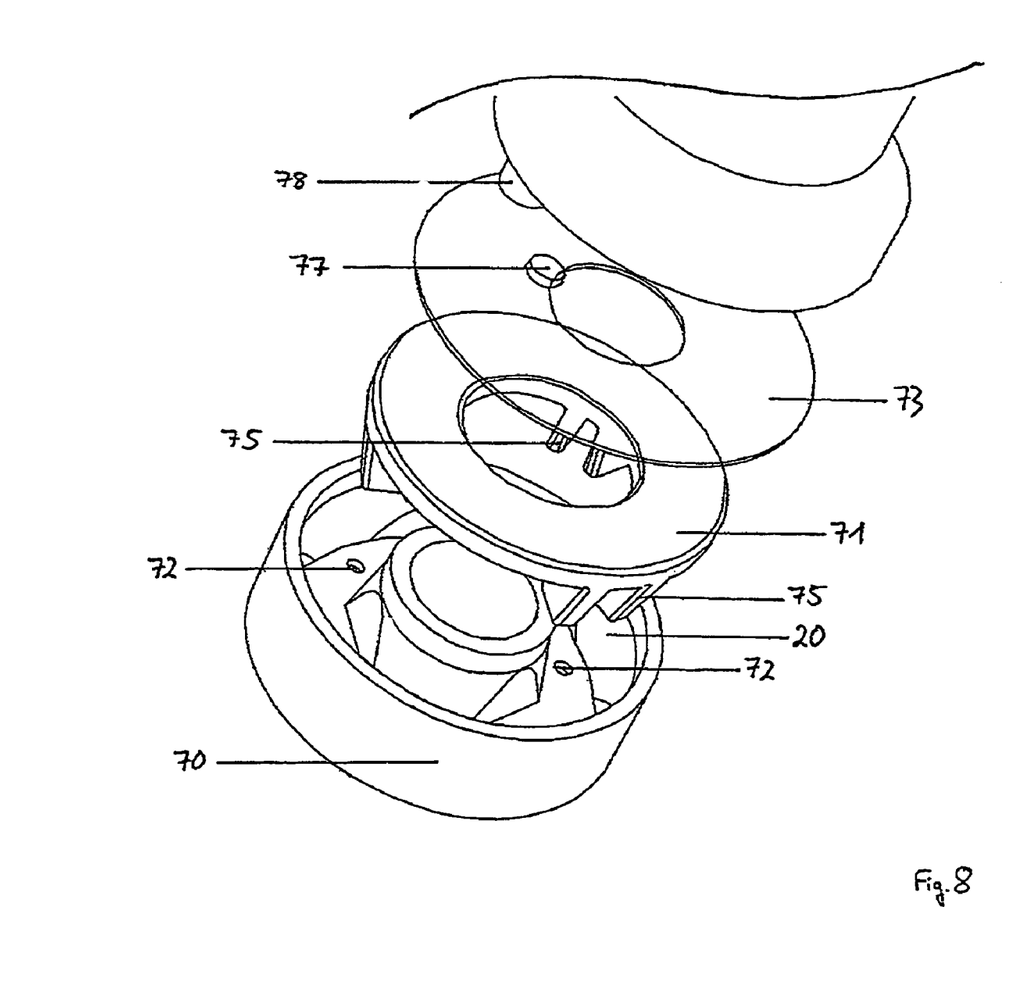
FIG. 8 a further perspective illustration of the embodiment according to FIG. 7.
Figure 9:
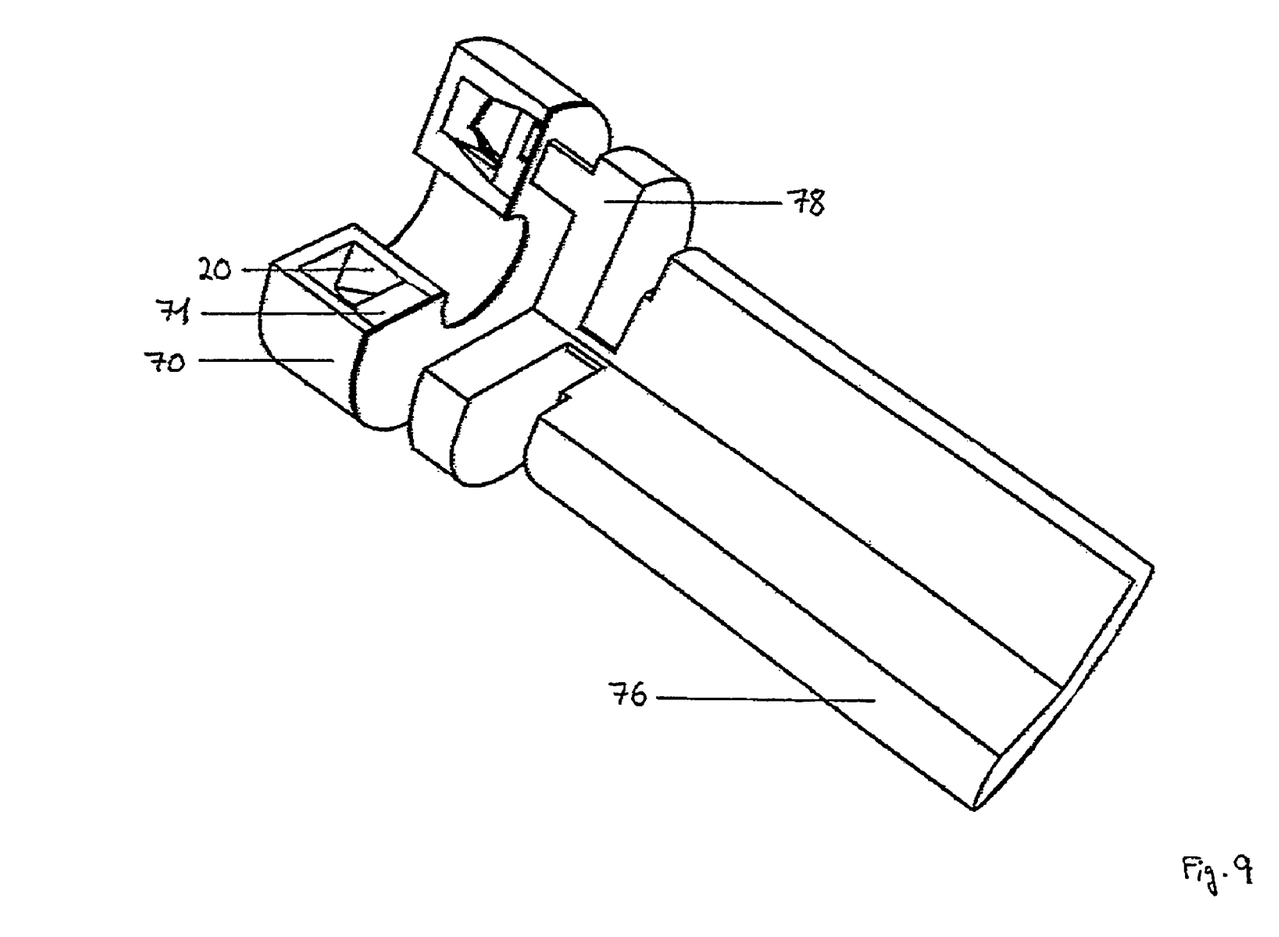
FIG. 9 yet another further perspective illustration of the embodiment according to FIG. 7.

FIGS. 7, 8 and 9 show another embodiment of a section of the handheld device 1 in a perspective view where pump pressure of a pump system is produced by means of a rotor component in a main body for the purpose of discharging the liquid active substance from the reservoir. In the FIGS. 7, 8 and 9 the same reference numbers as used for the same features, as in the preceding Figures.

The reservoir 20 is formed in a main body 70 and the pump system 21 coupled to the reservoir 20 has a rotatable rotor component 71 which, in the reservoir 20, is mounted with a stroke-over effect on one or several main body openings 72 during turning movement, where said main body openings 72 are connected to the fluid connection leading to the piercing device. With the stroke-over of the one or several main body openings 72, partial volumes of the liquid active substance are pressed into the main body openings 72 for the purpose of leading these partial volumes to the piercing device. The partial volumes are entrained by the rotor component 71 during the turning movement in the reservoir 20 and then pressed into the one or the several main body openings 72. The main body 70 with the reservoir 20 formed therein, the rotor component 71 and a sealing membrane 73 for sealing off the reservoir 20, where said membrane can be either adhesively applied or welded on for sealing purposes, each have a centrally located opening through which, depending on the design in each case, the piercing device and/or the coupling mechanism (not shown) are conducted.

On the rotatable rotor component 70, wing sections 75 are formed on a side 74 facing the one or several main body openings 72 which stroke over the main body openings 72. The reservoir 20 in the main body component 70 is sealed off at least liquid seal-tight against the ambient space by means of the sealing membrane 73. A drive 76 of the turning movement of the rotor component 71 shown schematically in the FIGS. 7, 8 and 9, and subsequently of the pressure application of the liquid active substance for discharge through the main body openings 72 is effected in a non-contacting mode wherein, at the rotor component 71, a magnetic component 77 is mounted which interacts with an allocated magnetic component 78 which, on its part, is turned in the process. The turning movement of the magnetic component 78 is produced with the drive which also drives the piercing device (not shown in the FIGS. 7, 8 and 9). To that extent, the drive 76 schematically shown in the FIGS. 7, 8 and 9 corresponds to the electric motor 4 in FIG. 1 above. In this way, the main body 70 can be integrated in the handheld device where, in this case, the needle module in FIG. 7 connects up on the left side.

The features of the invention as disclosed in this description, in the claims and in the drawings can be of significance both individually as well as in random combination for the realization of the invention in its various embodiments.

This application is based on European Patent Application No. 06015461.4 filed on Jul. 25, 2006, and the contents of which are incorporated hereinto by reference.

The invention claimed is:

1. A handheld device for the repetitive local puncturing of a skin for an input of a liquid active substance, particularly a permanent make-up and tattoo handheld device, comprising:
a piercing device formed in a needle module with repetitive movement forwards and backwards, in which the piercing device is driven by a drive unit formed in a drive module, a needle shaft coupled between the piercing device and the drive module so as to work as a coupling mechanism;

a reservoir for the liquid active substance, a portion of the reservoir being disposed in the needle module, a pump system directly attached to the reservoir where the pump system is configured in order to discharge the liquid active substance held in a cavity of the reservoir by a pressure application, a fluid connection running at least partially in a needle module casing where the fluid connection is configured in order to supply the liquid active substance from the reservoir to the piercing device, wherein, at the reservoir, an at least section-wise displaceable component is formed for the purpose of transmitting the pressure application generated by the pump apparatus to the liquid active substance, and wherein the at least section-wise displaceable component is an elastically deformable component and is executed as an elastic membrane, as desired.

2. The handheld device according to claim 1, wherein the reservoir extends along an axis running in the movement direction of the piercing device during the forward and backward movement.

3. The handheld device according to claim 1, wherein the fluid connection extends at least partially along the axis running in the movement direction of the piercing device during the forward and backward movement.

4. The handheld device according to claim 1, wherein the reservoir is formed at least partially encasing the axis running in the movement direction of the piercing device during the forward and backward movement.

5. The handheld device according to claim 1, wherein the fluid connection, at least with one section running in the needle module casing, is formed at least partially encasing the axis running in the movement direction of the piercing device during the forward and backward movement.

6. The handheld device according to claim 1, wherein the reservoir is detachably mounted and executed as a disposable reservoir, as desired.

7. The handheld device according to claim 6, wherein the reservoir is formed in a reservoir module detachably mounted and encasing at least parts of the pump system.

8. The handheld device according to claim 1, wherein the pump apparatus is separated in a fluid tight manner from the cavity holding the liquid active substance.

9. The handheld device according to claim 1, wherein the elastically deformable component is an elastically deformable wall section which is formed in the zone of the cavity, as desired.

10. The handheld device according to claim 1, wherein the at least section-wise displaceable component is formed at least partially encasing the axis running in the movement direction of the piercing device during the forward and backward movement.

11. The handheld device according to claim 1, wherein a push tappet of the pump system is allocated to the at least section-wise displaceable component.

12. The handheld device according to claim 11, wherein the push tappet is formed in the drive module.

13. The handheld device according to claim 11, wherein the push tappet is a ring tappet at least partially encasing the axis running in the movement direction of the piercing device during the forward and backward movement.

14. The handheld device according to claim 1, wherein the reservoir is formed in a main body and the pump system coupled to the reservoir has a rotatable rotor component which is mounted with a stroke-over effect on one or several main body openings during turning movement, where the main body openings are joined to the fluid connection.

15. The handheld device according to claim 1, wherein the pump system is configured in order to periodically transport the liquid active substance from the reservoir to the piercing device via the fluid connection.

16. The handheld device according to claim 1, further comprising:
a control apparatus coupled to the pump system is envisaged which is configured in order to excite the pump system in accordance with the repetitive forward and backward movement of the piercing device.

17. The handheld device according to claim 1, wherein the reservoir is completely formed in the needle module.

18. The handheld device according to claim 1, wherein the pump system implements at least one drive mechanism producing the pressure application, selected from the following group of drive mechanisms: piezo mechanism, magnetic drive mechanism and micro pump mechanism.

19. The handheld device according to claim 1, wherein the needle module is detachably coupled to the drive module and is executed as a disposable module, as desired.

20. The handheld device according to claim 1, wherein the fluid connection leads to at least one section of the piercing device, selected from the following sections of the piercing device: an outer needle surface, a needle intermediate space formed between several needles and an inner needle cavity.

21. A handheld device for the repetitive local puncturing of a skin for an input of a liquid active substance, particularly a permanent make-up and tattoo handheld device, comprising:
a needle module including:
a needle module casing,
a piercing device formed in the needle module casing and being capable of moving forwards and backwards with repetitive movement, and
a needle shaft coupled to the piercing device and the drive module;
a drive module including:
a drive unit providing forwards and backwards movement to the piercing device through the needle shaft;
a reservoir for receiving the liquid active substance, a portion of the reservoir being disposed in the needle module, and the portion of the reservoir disposed in the needle module being spaced from the needle shaft;
a pump system attached to the reservoir, wherein the pump system is configured to discharge the liquid active substance held in the reservoir by application of pressure;
a fluid connection running at least partially in the needle module casing where a fluid connection is configured in order to supply the liquid active substance from the reservoir to the piercing device,
wherein, at the reservoir, an at least section-wise displaceable component is formed for the purpose of transmitting the pressure application generated by the pump apparatus to the liquid active substance, and wherein the at least section-wise displaceable component is an elastically deformable component and is executed as an elastic membrane, as desired.

* * * * *